(12) United States Patent
Meyer

(10) Patent No.: US 7,533,709 B2
(45) Date of Patent: *May 19, 2009

(54) HIGH SPEED VACUUM PORTING

(75) Inventor: Thomas C. Meyer, Elkhart Lake, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 522 days.

This patent is subject to a terminal disclaimer.

(21) Appl. No.: 11/141,552

(22) Filed: May 31, 2005

(65) Prior Publication Data

US 2006/0266465 A1 Nov. 30, 2006

(51) Int. Cl.
*B32B 37/00* (2006.01)

(52) U.S. Cl. .................................. 156/517; 156/516

(58) Field of Classification Search ............... 156/265, 156/250, 510, 516, 517, 519, 521; 269/21
See application file for complete search history.

(56) References Cited

U.S. PATENT DOCUMENTS

| 135,145 | A | 1/1873 | Murphy |
|---|---|---|---|
| 293,353 | A | 12/1884 | Purvis |
| 312,257 | A | 2/1885 | Cotton et al. |
| 410,123 | A | 8/1889 | Stilwell |
| 432,742 | A | 7/1890 | Stanley |
| 643,821 | A | 2/1900 | Howlett |
| 1,393,524 | A | 10/1921 | Grupe |
| 1,605,842 | A | 11/1926 | Jones |
| 1,686,595 | A | 10/1928 | Belluche |
| 1,957,651 | A | 5/1934 | Joa |
| 2,009,857 | A | 7/1935 | Potdevin |
| 2,054,832 | A | 9/1936 | Potdevin |
| 2,117,432 | A | 5/1938 | Linscott |
| 2,128,746 | A | 8/1938 | Joa |
| 2,131,808 | A | 10/1938 | Joa |
| 2,164,408 | A | 7/1939 | Joa |
| 2,167,179 | A | 7/1939 | Joa |
| 2,171,741 | A | 9/1939 | Cohn et al. |
| 2,213,431 | A | 9/1940 | Joa |

(Continued)

FOREIGN PATENT DOCUMENTS

BE 1007854 11/1995

(Continued)

OTHER PUBLICATIONS

Reciprocating Mechanisms, Ingenious Mechanisms for Designers and Inventors, Franklin Jones vol. 1.

*Primary Examiner*—James Sells
(74) *Attorney, Agent, or Firm*—Ryan Kromholz & Manion S.C.

(57) ABSTRACT

This invention proposes a new, improved method and apparatus for applying web segments to a traveling web. These web segments, sometimes called ears or wings, may be asymmetrical or otherwise incompatible with the usual slip-and-cut method. The asymmetrical shape may have differing web tensions which can cause the web segments to be improperly engaged with the vacuum holes on an anvil roll. The present invention utilizes both circumferential rows of vacuum holes and an additional pattern of ear retaining vacuum holes. The circumferential rows of vacuum holes are activated consecutively by vacuum commutation, however, the pattern of ear retaining vacuum holes are activated simultaneously to counter the effects of differing web tensions on the ear portions.

3 Claims, 3 Drawing Sheets

U.S. PATENT DOCUMENTS

| | | |
|---|---|---|
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A * | 11/1976 | Farish .................. 493/430 |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,672,705 A | 6/1987 | Bors et al. |

| Patent | Date | Name |
|---|---|---|
| 4,675,062 A | 6/1987 | Instance |
| 4,693,056 A | 9/1987 | Raszewski |
| 4,701,239 A | 10/1987 | Craig |
| 4,726,874 A | 2/1988 | Van Vliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Invine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,510 A | 1/1989 | Wittrock et al. |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,925,520 A | 5/1990 | Beaudoin et al. |
| 4,927,322 A | 5/1990 | Schweizer et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,203,043 A | 4/1993 | Riedel |
| 5,213,645 A | 5/1993 | Nomura et al. |
| 5,223,069 A | 6/1993 | Tokuno et al. |
| 5,226,992 A | 7/1993 | Morman |
| 5,246,433 A | 9/1993 | Hasse et al. |
| 5,267,933 A | 12/1993 | Precoma |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,531,850 A | 7/1996 | Herrmann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,602,747 A | 2/1997 | Rajala |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| RE35,687 E | 12/1997 | Igaue et al. |
| 5,693,165 A | 12/1997 | Schmitz |
| 5,699,653 A | 12/1997 | Hartman et al. |
| 5,707,470 A | 1/1998 | Rajala et al. |
| 5,711,832 A | 1/1998 | Glaug et al. |
| 5,725,518 A | 3/1998 | Coates |
| 5,745,922 A | 5/1998 | Rajala et al. |
| 5,746,869 A | 5/1998 | Hayden et al. |
| 5,749,989 A | 5/1998 | Linman et al. |
| 5,788,797 A | 8/1998 | Herrin et al. |
| 5,817,199 A | 10/1998 | Brennecke et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,970 A | 10/1999 | Woolwine et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,183,576 B1 | 2/2001 | Couillard et al. |
| 6,210,386 B1 | 4/2001 | Inoue |
| 6,212,859 B1 | 4/2001 | Bielik, Jr. et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |

| | | | | | |
|---|---|---|---|---|---|
| 6,478,786 B1 | 11/2002 | Gloug et al. | 2007/0074953 A1 | 4/2007 | McCabe |
| 6,482,278 B1 | 11/2002 | McCabe et al. | | | |
| 6,494,244 B2 | 12/2002 | Parrish et al. | FOREIGN PATENT DOCUMENTS | | |
| 6,521,320 B2 | 2/2003 | McCabe et al. | CA | 1146129 | 5/1983 |
| 6,524,423 B1 | 2/2003 | Hilt et al. | CA | 1153345 | 9/1983 |
| 6,551,228 B1 | 4/2003 | Richards | CA | 1190078 | 7/1985 |
| 6,551,430 B1 | 4/2003 | Glaug et al. | CA | 1210744 | 9/1986 |
| 6,554,815 B1 | 4/2003 | Umebayashi | CA | 1212132 | 9/1986 |
| 6,572,520 B2 | 6/2003 | Blumle | CA | 1236056 | 5/1988 |
| 6,581,517 B1 | 6/2003 | Becker et al. | CA | 1249102 | 1/1989 |
| 6,596,108 B2 | 7/2003 | McCabe | CA | 1292201 | 11/1991 |
| 6,605,172 B1 | 8/2003 | Anderson et al. | CA | 1307244 | 9/1992 |
| 6,605,173 B2 | 8/2003 | Glaug et al. | CA | 1308015 | 9/1992 |
| 6,637,583 B1 | 10/2003 | Andersson | CA | 1310342 | 11/1992 |
| 6,648,122 B1 | 11/2003 | Hirsch et al. | CA | 2023816 | 3/1994 |
| 6,649,010 B2 * | 11/2003 | Parrish et al. ............... 156/265 | CA | 2404154 | 10/2001 |
| 6,659,150 B1 | 12/2003 | Perkins et al. | CA | 2541194 | 1/2006 |
| 6,659,991 B2 | 12/2003 | Suckane | CA | 2559517 | 5/2007 |
| 6,675,552 B2 | 1/2004 | Kunz et al. | DE | 102006047280 | 4/2007 |
| 6,684,925 B2 | 2/2004 | Nagate et al. | EP | 0044206 | 1/1982 |
| 6,766,817 B2 | 7/2004 | da Silva | EP | 0048011 | 3/1982 |
| D497,991 S | 11/2004 | Otsubo et al. | EP | 0089106 | 9/1983 |
| 6,820,671 B2 | 11/2004 | Calvert | EP | 0304140 | 8/1987 |
| 6,837,840 B2 | 1/2005 | Yonekawa et al. | EP | 0439897 | 2/1990 |
| 6,840,616 B2 | 1/2005 | Summers | EP | 0 439 897 A1 * | 8/1990 |
| 6,852,186 B1 | 2/2005 | Matsuda et al. | EP | 0455231 | 11/1991 |
| 6,875,202 B2 | 4/2005 | Kumasaka et al. | EP | 510251 | 10/1992 |
| 6,893,528 B2 | 5/2005 | Middelstadt et al. | EP | 0652175 | 5/1995 |
| 6,918,404 B2 | 7/2005 | Dias da Silva | EP | 0811473 | 12/1997 |
| 6,978,486 B2 | 12/2005 | Zhou et al. | EP | 0901780 | 3/1999 |
| 7,066,586 B2 | 6/2006 | da Silva | EP | 990588 | 4/2000 |
| 7,077,393 B2 | 7/2006 | Ishida | EP | 1132325 | 9/2001 |
| 7,172,666 B2 * | 2/2007 | Groves et al. ............... 156/64 | EP | 1272347 | 1/2003 |
| 7,214,174 B2 | 5/2007 | Allen et al. | EP | 1571249 | 9/2005 |
| 7,247,219 B2 | 7/2007 | O'Dowd | EP | 1619008 | 1/2006 |
| 2001/0012813 A1 | 8/2001 | Bluemle | EP | 1707168 | 4/2006 |
| 2001/0017181 A1 | 8/2001 | Otruba et al. | ES | 509706 | 11/1982 |
| 2002/0046802 A1 | 4/2002 | Tachibana et al. | ES | 520559 | 12/1983 |
| 2002/0059013 A1 | 5/2002 | Rajala et al. | ES | 296211 | 12/1987 |
| 2003/0000620 A1 | 1/2003 | Herrin et al. | FR | 2255961 | 7/1975 |
| 2003/0015209 A1 | 1/2003 | Gingras et al. | FR | 0206208 | 12/1986 |
| 2003/0052148 A1 | 3/2003 | Rajala et al. | FR | 2891811 | 4/2007 |
| 2003/0066585 A1 | 4/2003 | McCabe | GB | 191101501 | 1/1911 |
| 2003/0083638 A1 | 5/2003 | Malee | GB | 439897 | 12/1935 |
| 2003/0084984 A1 | 5/2003 | Glaug et al. | GB | 1126539 | 9/1968 |
| 2003/0089447 A1 | 5/2003 | Molee et al. | GB | 1346329 | 2/1974 |
| 2003/0135189 A1 | 7/2003 | Umebayashi | GB | 1412812 | 11/1975 |
| 2004/0007328 A1 | 1/2004 | Popp et al. | GB | 2045298 | 10/1980 |
| 2004/0016500 A1 | 1/2004 | Tachibana et al. | GB | 2288316 | 10/1995 |
| 2004/0112517 A1 | 6/2004 | Groves et al. | JP | 428364 | 1/1992 |
| 2004/0164482 A1 | 8/2004 | Edinger | JP | 542180 | 2/1993 |
| 2005/0000628 A1 | 1/2005 | Norrley | JP | 576566 | 3/1993 |
| 2005/0196538 A1 | 9/2005 | Sommer et al. | JP | 626160 | 2/1994 |
| 2005/0230056 A1 | 10/2005 | Meyer et al. | JP | 626161 | 2/1994 |
| 2005/0230449 A1 | 10/2005 | Meyer et al. | JP | 6197925 | 7/1994 |
| 2005/0233881 A1 | 10/2005 | Meyer | JP | 10035621 | 2/1998 |
| 2005/0234412 A1 | 10/2005 | Andrews et al. | JP | 10-277091 | 10/1998 |
| 2005/0257881 A1 | 11/2005 | Coose et al. | SE | 0602047 | 5/2007 |
| 2005/0275148 A1 | 12/2005 | Beaudoin et al. | WO | WO 9747810 | 12/1997 |
| 2006/0021300 A1 | 2/2006 | Tada et al. | WO | WO9907319 | 2/1999 |
| 2006/0137298 A1 | 6/2006 | Oshita et al. | WO | WO9913813 | 3/1999 |
| 2006/0224137 A1 | 10/2006 | McCabe et al. | WO | WO9965437 | 12/1999 |
| 2006/0265867 A1 | 11/2006 | Schaap | WO | WO0143682 | 6/2001 |
| | | | WO | WO0172237 | 10/2001 |
| | | | WO | WO2005075163 | 1/2005 |

* cited by examiner

HIGH SPEED VACUUM PORTING

BACKGROUND OF THE INVENTION

The present invention relates to disposable hygiene products and more specifically, to methods and apparatuses for processing disposable hygiene products. More specifically, the invention relates to cutting and applying segments of one web to attach to a disposable hygiene product. Various types of automatic manufacturing equipment have been developed which produce the desired results with a variety of materials and configurations.

When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Typical vacuum rolls used in the prior art have rows of vacuum holes which are fed by cross-drilled ports, each being exposed to the source of vacuum by commutations, as the ports move into a zone of negative pressure in a stationary manifold. Such a configuration serves to apply vacuum sequentially to each successive row of holes.

A common problem associated with slip-and-cut applicators occurs at the point of cut. Since the web being cut is traveling at a very low velocity compared to the anvil and knife velocity (perhaps ½0th), the engagement of the knife with infeeding web tends to induce a high tensile stress in the infeeding web. Having been placed under such a high level of stress, the infeeding web can recoil violently when the cut is finally completed, causing loss of control of the infeeding web. This "snap-back" effect increases with the thickness of the infeeding web. Thicker webs tend to prolong the duration of engagement with the knife before completion of the cut, thereby increasing the build-up of stress. This is a common process problem that is usually addressed by the provision of various shock-absorbing devices. One possible solution might have been to reduce the surface velocity of the knife, but substantially different velocities between the knife and anvil result in rapid wear of the knife edge and/or anvil face, depending on relative hardness.

Continual improvements and competitive pressures have incrementally increased the operational speeds of disposable diaper converters. As speeds increased, the mechanical integrity and operational capabilities of the applicators had to be improved accordingly. As a further complication, the complexity of the fastener tabs being attached to those products has also increased. Consumer product manufacturers are now offering tapes which are die-cut to complex profiles and which may be constructed of materials incompatible with existing applicators. For instance, a proposed fastener tab may be a die-profiled elastic textile, instead of a typical straight-cut stiff-paper and plastic type used in the past. Consequently, a manufacturer may find itself with a slip-and-cut applicator which cannot successfully apply die-cut tape segments. Existing applicators cannot successfully apply fastener whose boundaries are fully profiled, as may be desired to eliminate sharp corners, which might irritate a baby's delicate skin. This demonstrates a clear need for an improved applicator capable of applying new fastener configurations and overcoming other shortcomings of prior art applicators.

Slip-and-cut apparatus are well known for their ability to cut relatively short segments of one web and place them accurately on another, higher speed web. Certain materials, however, behave badly in these applications. The tension pulsation caused by the cutting may cause the material to snap back, losing its natural track down the moving surface of the anvil roll. This is especially common with thick webs. Other materials, such as nonwoven fabrics, may be difficult to control because they are very porous and provide little resistance to air flow to keep the material on track. Still other materials, such as certain perforated films may possess texture qualities which tend to be very unstable on the anvil surface, acting instead like a puck on an air hockey table.

These problems are further exacerbated by using materials with a very low modulus of elasticity. Here, even very low levels of vacuum at the anvil surface may cause the material to stretch with the advancing movement of the anvil. The sudden change of tension seen when the knife cuts this over-stretched web can result in severe snap-back and complete loss of position, relative to the intended centerline. Likewise, webs with very high moduli may snap back violently when the web is cut.

The prior art is quite successful when processing full-width or symmetrical webs, which are drawn uniformly forward by the sliding vacuum surface on which they are held. Attempts to process asymmetrical webs on such a surface are less successful, as the draw of the advancing vacuum pattern will act differently on parts of the web which have differing lines of tension. For instance, a die-cut ear web for a disposable diaper may have only a narrow continuous portion along one edge, with the opposite edge being more or less scalloped in shape.

It is therefore an object of this invention to provide an apparatus which can maintain control over die cut web sections of various shapes.

SUMMARY OF THE INVENTION

The present invention provides a method and apparatus which provides high speed vacuum porting to selected vacuum pattern areas on a rotating cylindrical roll. This invention has the advantage of being able to "switch on" selected areas rather than discrete rows.

In a typical configuration of a slip-and-cut applicator, there is a pattern of vacuum holes distributed to evenly draw the entering web onto the anvil's surface and thence into a cut point where a knife edge engages an anvil, thus severing the web into discrete segments if so desired. The invention provides a generally cylindrical anvil body connected to a source of vacuum. The anvil roll has an ear retaining portion on its outer surface. This ear retaining portion is formed with a plurality of vacuum holes. A vacuum slot is provided on an end face surface (commutating surface) of the anvil roll and is adapted to put the plurality of vacuum holes in communication with the vacuum source. The anvil roll is utilized in connection with a rotary knife to cut small segments of an incoming web. The anvil roll then transfers those cut segments to an additional web.

It is desired to immediately grasp and hold the ear at the instant of the cut of the continuous web as it is separated into discrete segments. As soon as the ear is cut from the infeeding web, instantaneous control must be established.

One embodiment of this invention provides a cylindrical anvil roll which is symmetrical about a center circumferential plane. This embodiment allows two incoming webs to be utilized, allowing two segments to be cut, one on either end of the anvil roll, each time the rotary knife engages the anvil roll.

Additionally, the anvil roll may have an additional set of ear retaining portions formed in diametric opposition to the first set of ear retaining portions. In such an embodiment, the knife roll would engage the anvil roll two times for each rotation of the anvil roll, thus producing up to four cut segments per rotation of the anvil roll.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
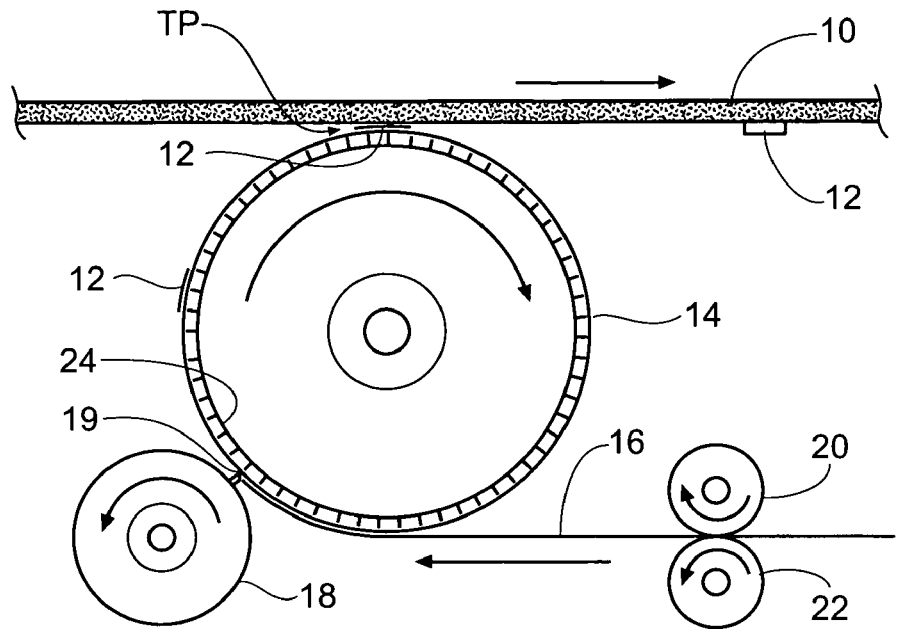
FIG. 1 is a diagrammatic side view of a Prior Art process.

Referring to the drawings there is seen in FIG. 1 a diagrammatic illustration of a prior art process for applying tabs to webs in a diaper making process. The present invention can use this prior art method of affixing the ears 12 to the web 10, with a different anvil, the new anvil 114 described below. Web 10 is a composite material used in formation of diapers which is generally formed of various layers of material such as plastic back sheets, absorbent pads and nonwoven topsheets. A series of ears 12 are applied to web 10. In the illustrated process a rotatable vacuum anvil 14 is used to supply the ears 12 to web 10. Anvil 14 has internally reduced air pressure or vacuum (not shown), and a plurality of openings 24 are provided through its surface to enable suction of the tab segments 13 against the anvil surface 14. A web of the ear tab forming material 16 is fed by rollers 20 and 22 against the anvil surface 14 where it is cut into segments by a rotary knife 18.

In the prior art, the surface of the anvil roll 14 has vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

It can be seen from FIG. 1 that in the prior art, the infeed of the ear tab forming material 16 can be at a first speed (with individual ears 12 spaced together), after which the individual ears gain speed to the speed of the anvil 14. Typical infeed speeds could be 120 mm/product for the infeed, while anvil speeds could be 450 mm/product on the anvil. This transition from the slower first speed to the quicker second speed takes place at the cut point, the ear tab forming material 16 slipping on the anvil 14 until cut. However, immediately at the transition cut point 19 from the slower speed to the faster speed, it is desired to place vacuum on the ears because centrifugal force would try to throw the ears off of the vacuum anvil 14.

Figure 2:
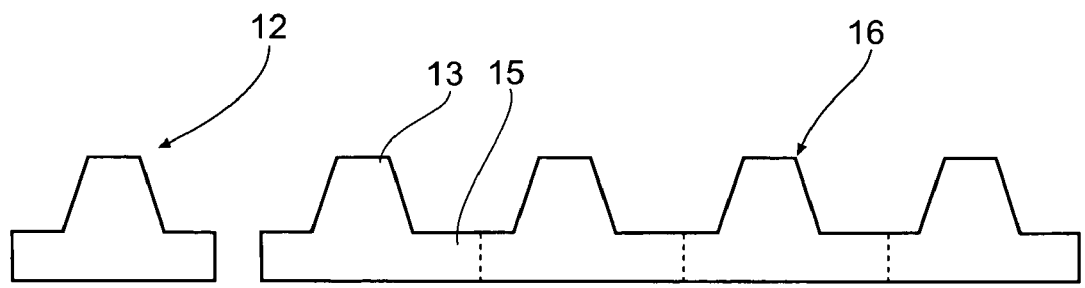
FIG. 2 is a top view of the ear forming web including an individual ear detached from the web.

In both the prior art and the present invention, a continuous ear forming web 16 is provided to the system. The web 16 is comprised of two portions 13 and 15, as shown in FIG. 2. Segment 13 is more specifically referred to as the tab section of the ear 12, segment 15 is the ribbon section of the ear 12. The ear forming material 16 is cut into individual ears 12 by the rotary knife 18 as shown in FIG. 1, along lines such as the dashed lines shown in FIG. 2.

Figure 3:
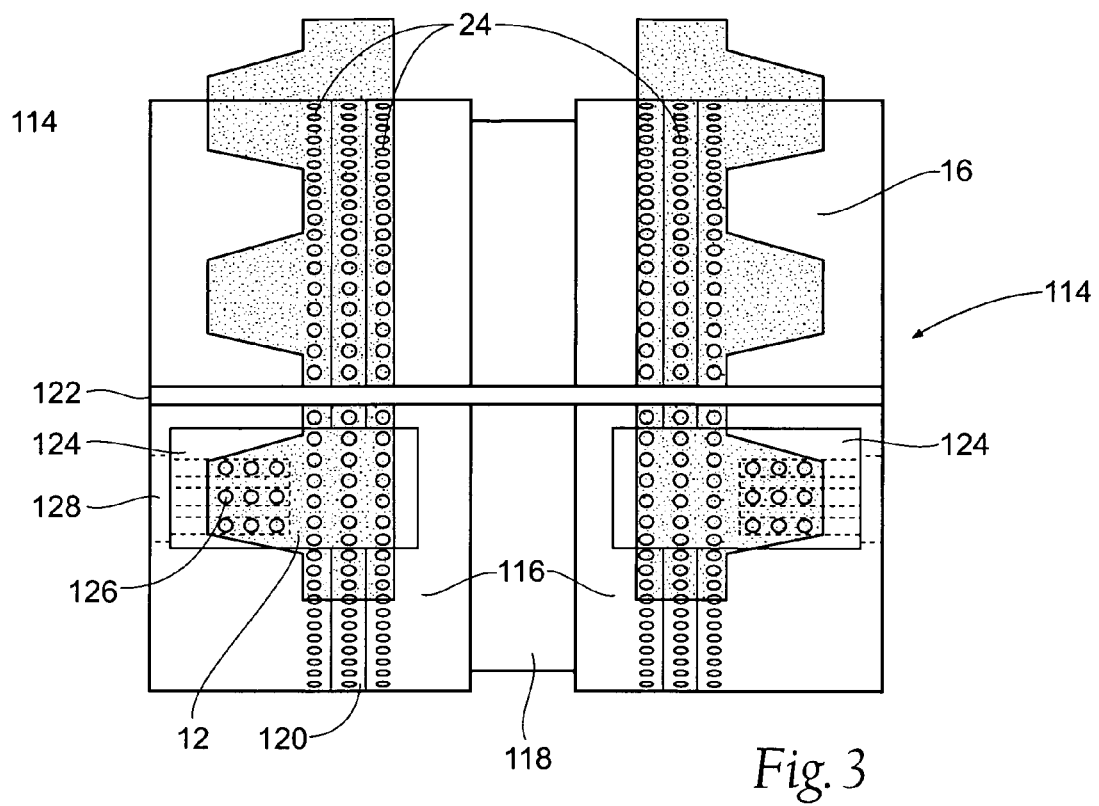
FIG. 3 is a front view of the anvil roll of the present invention.

Referring now to FIG. 3, a front view of an anvil roll 114 of the present invention is shown carrying ear forming material 16 (and later, an ear 12) in phantom. The anvil roll 114 is preferably formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

The preferred embodiment of the anvil roll 114 of the present invention is also formed with two diametrically opposed anvil pockets 122 and two diametrically opposed pairs of ear retaining portions 124. The ear retaining portions can be created as inserts, with different vacuum patterns applied as the user deems necessary. Each anvil pocket 122 is a groove which extends across the face of the entire anvil roll 114. One ear retaining portion 124 is located on each of the vacuum portions 116. Each ear retaining portion 124 has an ear vacuum hole pattern 126 made of a plurality of vacuum holes 24 located at or near the surface of the anvil roll 144. The preferred embodiment, as shown in FIG. 3 is a plurality of rows of vacuum holes 24, each row having a plurality of vacuum holes 24, although more or less than those configurations or patterns shown can be used.

In operation, two webs of ear material 16 are carried by the anvil 114. One web of ear material 16 is located on each vacuum portion 116. A single ear 12 is cut from the ear web 16 when the rotary knife 18 engages the anvil roll 114 at the anvil pocket 122. Immediately after a single ear 12 is cut from the ear web 16, the single ear 12 is located on the ear retaining portion 124, particularly the tab portion 13 of the ear 12 as shown in FIG. 2. At this point the vacuum in the ear retaining portion 124 has been engaged to secure the single ear 12 to the anvil roll 114. As the anvil roll 114 rotates the vacuum is released at a predetermined location so that the single ear 12 can be applied to the diaper web 10. Because this configuration has two vacuum portions 116, a pair of two ears 12 is cut each time the rotary knife 18 engages the anvil toll 114. This allows for two pair of ears 12 to be cut with each revolution of the anvil roll 114. Shown in dotted line in FIG. 3 is a vacuum slot 128, described below.

Figure 4:
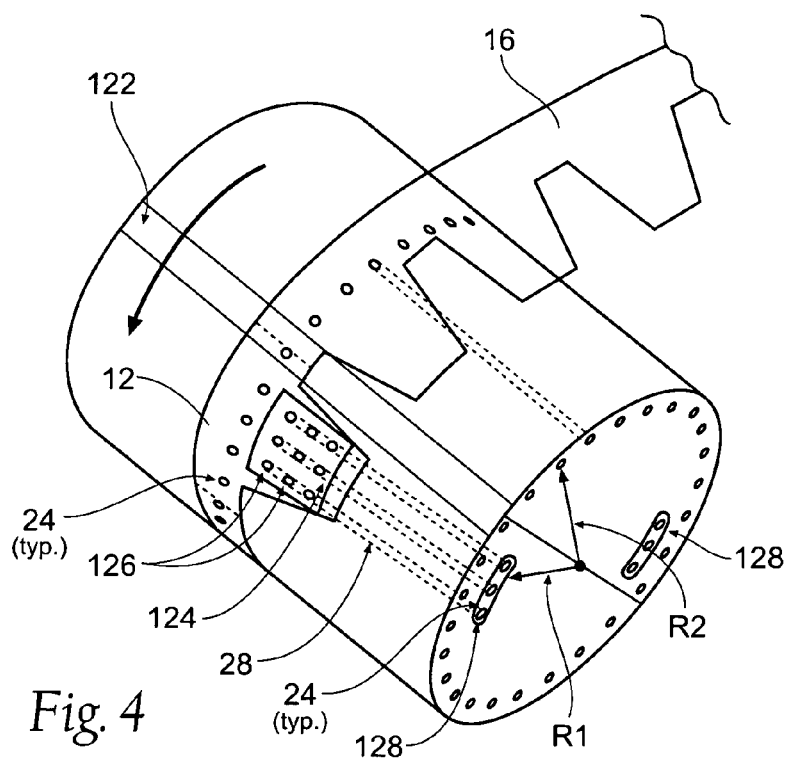
FIG. 4 is a perspective view of the anvil roll of the present invention.

Referring now to FIG. 4, a perspective view of the anvil 114 is shown. The anvil 114 will be described in relation to its endface and its outer surface, the outer surface that surface shown on FIG. 3 and the endface the two ends of the anvil 114.

The vacuum slot 128 contains a plurality of vacuum holes 24 that allow commutation of the vacuum to the entire ear vacuum hole pattern 126, allowing the pattern 126 to be activated simultaneously, as opposed to each of the rows that comprise the vacuum of vacuum holes 24 being enabled one at a time. The vacuum pattern 126 is activated utilizing drilled ports 28 that communicate the vacuum from the slot 128 to the individual holes 24 of the pattern 126. It should be noted that the pattern 126 can also be provided with a depressed slot configuration so that it too is all simultaneously enabled with vacuum.

The remaining vacuum holes 24 provided on the anvil roll 114 are enabled sequentially, by known vacuum commutation method utilizing cross drilled ports 28.

The vacuum slot 128 is provided at a first radius R1 on the anvil roll 114, the remaining vacuum holes provided at a different R2. The differing radii R1 and R2 allow two vacuum manifolds (not shown) to communicate each at a different radius, R1 or R2, thus selectively applying vacuum to the anvil.

Figure 5:
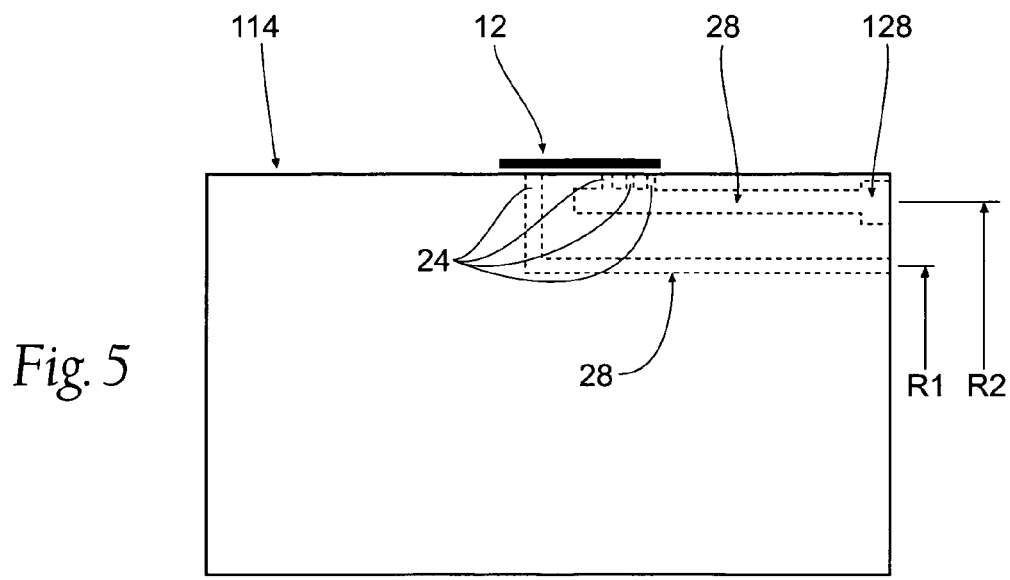
FIG. 5 is a cross sectional view of the anvil roll of the present invention.

Referring now to FIG. 5, a cross sectional view of the anvil roll 114 of the present invention. In this embodiment, the slot 128 has been placed at R2. It is appreciated that the slot 128 communicating with the pattern 126 can be placed at either R1 or R2, and the remaining vacuum holes 24 communicating with drilled ports 28 can be interchanged at either R1 or R2. For machining purposes, it is likely preferable to place the slot 128 communicating with the pattern at R2 for simplicity in machining.

Figure 6:
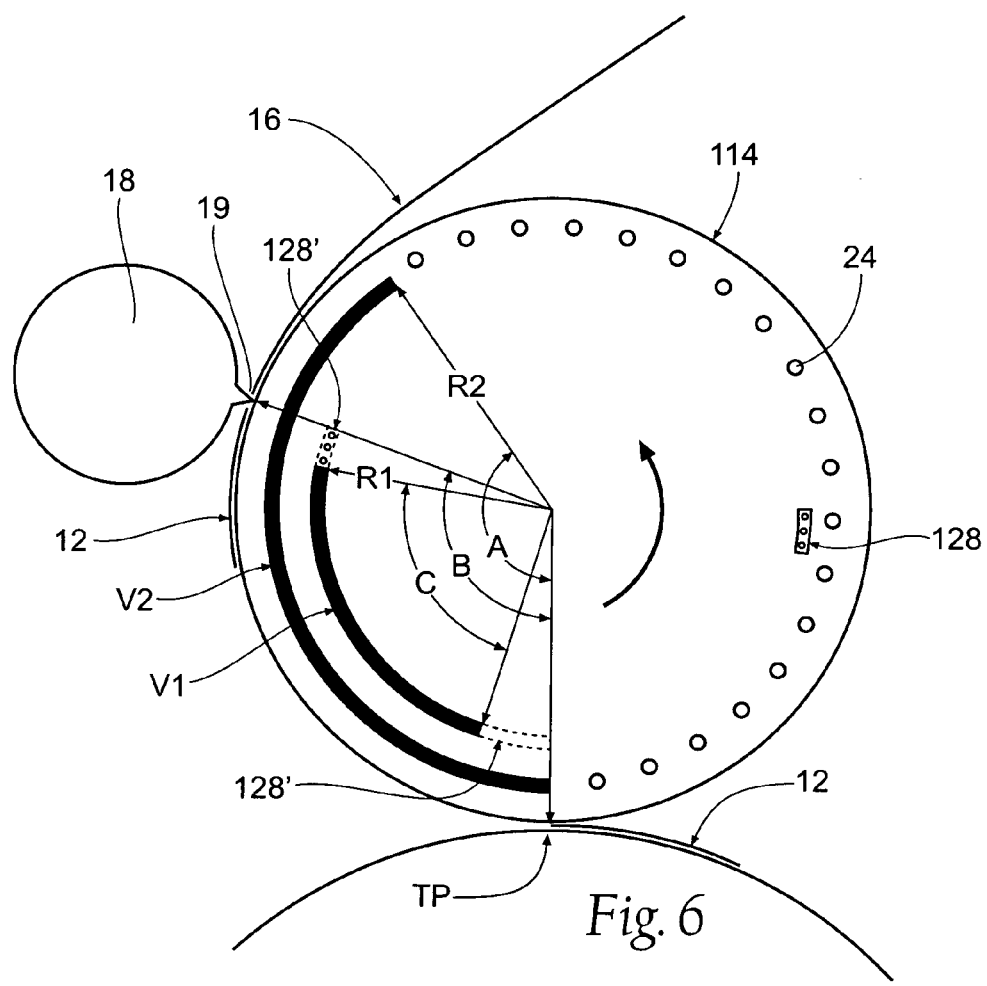
FIG. 6 is a side view of the anvil roll of the present invention, showing an endface of the anvil, and a vacuum manifold pattern applied to vacuum holes disposed on the endface of the anvil.

Referring now to FIG. 6, a side view of the anvil roll 114 is shown, showing the endface of the anvil, or the circular portion of the cylindrical body 114. The ear web 16 is shown infeeding to the anvil 114, where it is then cut with the rotary knife 18. It is desired to apply the vacuum to the pattern 126 simultaneously with the knife cut.

The range of vacuum application is provided for with a manifold (not shown) that continuously applies vacuum to vacuum patterns V1 and V2. Vacuum pattern V1 is at R1, Vacuum pattern V2 is at R2. Vacuum pattern V1 applies vacuum to the slot 128 each time the slot 128 rotates through the vacuum pattern V1 provided on the manifold. When the slot 128 is in communication with V1, vacuum is applied to vacuum holes 24 associated in the slot 128 on the endface of the anvil for commutation to the pattern 126 on the outer surface of the anvil 114. When the slot 128 is not in communication with V1, the vacuum to the pattern 126 is turned off.

Vacuum pattern V2 is applied to the vacuum holes 24 disposed on the endface of the anvil 114 and the associated circumferential ribbon vacuum hole pattern on the outer surface of the anvil 114 throughout V2. As each successive vacuum hole 24 rotates through V2, the vacuum is on. As each successive vacuum hole 24 leaves V2, its vacuum is turned off.

From the center of the endface, a radius extending to the contact point of the knife 18 with the anvil roll 114 can be extended, and as the anvil roll rotates through angle B as shown, the rotation of the ear 12 will be from the knife point to the transfer point TP. It is throughout this angle B that vacuum is desired across the pattern 126 and onto the ear 12. To accomplish this, a smaller angle C has vacuum applied to it. The angle C can be expressed mathematically as the angle B minus twice the width 128' of the slot 128. This is because pattern 126 is placed in communication with the slot 128, the slot 128 communicates vacuum simultaneously to the pattern 126. Therefore, the leading edge of the ear 12 and the trailing edge of the ear 12 will receive vacuum at the same time. Therefore, the user must allow the leading edge of the ear 12 to pass by the knife 18 the desired length of the ear 12 prior to engaging the vacuum onto the ear 12. Similarly, prior to arriving at the transfer point TP, the vacuum will have to be released on both the leading and trailing edges of the ear 12 simultaneously, allowing the ear 12 to continue on its downstream path.

An angle A, larger than angle B, is provided to define V2, as it is desired to draw the web 16 into contact with the anvil both prior to and during cutting by the knife 18.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An anvil roll comprising:
    a cylindrical body having an end face and an outer surface, said outer surface engaging a traveling web;
    a slot created on said end face at a first radius from the center of said end face;
    a first plurality of vacuum holes disposed in said slot;
    a second plurality of vacuum holes at a second radius from the center of said end face;
    said first plurality of vacuum holes coupled with an ear pattern vacuum array on said outer surface;
    said second plurality of vacuum holes coupled with a ribbon pattern vacuum array on said outer surface.

2. An anvil roll according to claim 1, said ear pattern vacuum array comprising a plurality of rows and a plurality of columns sized smaller than an ear piece of ribbon.

3. An anvil roll according to claim 1, said ribbon pattern vacuum array comprising a circumferential plurality of vacuum holes.

* * * * *